(12) United States Patent
Masri et al.

(10) Patent No.: US 9,693,981 B2
(45) Date of Patent: Jul. 4, 2017

(54) ZALEPLON GASTRORETENTIVE DRUG DELIVERY SYSTEM

(75) Inventors: Suher Masri, Jerusalem (IL); Eytan Moor, Jerusalem (IL); David Kirmayer, Jerusalem (IL); Elena Kluev, Jerusalem (IL); Giora Carni, Jerusalem (IL); Nadav Navon, Jerusalem (IL)

(73) Assignee: INTEC PHARMA LTD., Jerusalem (IL)

(*) Notice: Subject to any disclaimer, the term of this patent is extended or adjusted under 35 U.S.C. 154(b) by 163 days.

(21) Appl. No.: 13/132,899

(22) PCT Filed: Oct. 19, 2009

(86) PCT No.: PCT/IB2009/007731
§ 371 (c)(1),
(2), (4) Date: Sep. 20, 2011

(87) PCT Pub. No.: WO2010/064139
PCT Pub. Date: Jun. 10, 2010

(65) Prior Publication Data
US 2012/0021051 A1    Jan. 26, 2012

Related U.S. Application Data

(60) Provisional application No. 61/120,051, filed on Dec. 4, 2008.

(51) Int. Cl.
| A61K 9/56 | (2006.01) |
| A61P 25/20 | (2006.01) |
| A61K 9/00 | (2006.01) |
| A61K 9/52 | (2006.01) |
| A61K 31/519 | (2006.01) |
| A61K 31/195 | (2006.01) |
| A61K 9/48 | (2006.01) |
| A61K 9/70 | (2006.01) |

(52) U.S. Cl.
CPC .......... *A61K 31/195* (2013.01); *A61K 9/0065* (2013.01); *A61K 9/4808* (2013.01); *A61K 9/7007* (2013.01)

(58) Field of Classification Search
CPC ......... A61P 25/20; A61K 31/519; A61K 9/56; A61K 9/00; A61K 9/0065; A61K 9/7007; A61K 31/195; A61K 9/4808
See application file for complete search history.

(56) References Cited

U.S. PATENT DOCUMENTS

| 4,767,627 A | 8/1988 | Caldwell et al. |
| 6,485,746 B1 * | 11/2002 | Campbell et al. ............ 424/468 |
| 6,605,300 B1 | 8/2003 | Burnside et al. |
| 6,685,962 B2 | 2/2004 | Friedman et al. |
| 2003/0013726 A1 | 1/2003 | Selzer |
| 2004/0180088 A1 | 9/2004 | Dudhara et al. |
| 2004/0224020 A1 * | 11/2004 | Schoenhard ................. 424/471 |
| 2005/0136109 A1 | 6/2005 | Rowley et al. |
| 2005/0244517 A1 | 11/2005 | Hall et al. |
| 2006/0024365 A1 | 2/2006 | Vaya et al. |
| 2008/0020039 A1 | 1/2008 | Parikh et al. |
| 2010/0305208 A1 | 12/2010 | Dudhara et al. |

FOREIGN PATENT DOCUMENTS

| CN | 1520286 A | 8/2004 |
| WO | WO-0100181 A2 | 1/2001 |
| WO | WO 2007/083309 A2 | 7/2007 |
| WO | WO 2007/093999 A1 | 8/2007 |
| WO | WO-2008110577 A1 | 9/2008 |

OTHER PUBLICATIONS

The International Search Report received in the parent application No. PCT/IB2009/007731, dated Septmber 10, 2010.
The Office Action received in the related U.S. Appl. No. 12/797,441, dated May 22, 2012.
Morris, et al., "Effects of Written Drug Information on Patient Knowledge and Compliance: A Literature Review", *Am J Public Health*, 1979, vol. 69, No. 1, pp. 47-52.
Tom, et al., "Applications of Supercritical Fluids in the Conrtolled Release of Drugs", Supercritical Fluid Engineering Science, Chapter 19, pp. 238-257, ACS Symposium Series, vol. 514, Publication date (Print): Dec. 17, 1962.
Danjou, et al., "A comparison of the residual effects of zaleplon and zolpidem following administration 5 to 2 h before awakening", *J Clin Pharmacol*, 1999, vol. 48, pp. 367-374.
Greenblatt et al., "Pharmacokinetic profile of SKP-1041, a modified release formulation of zaleplon" Biopharm. Drug Dispos, pp. 1-9 (2011).
Greenblatt et al., "Phase I, Randomized, Double-Blind, Placebo-Controlled, Crossover Study to Compare the Pharmacokinetics of a Single Oral Dose of a New Zaleplon Formulation (SKP-1041) and Open-Label Zaleplon in Healthy Elderly Subjects" Poster Presented at Sleep on Jun. 9, 2010 in San Antonio, TX.

(Continued)

*Primary Examiner* — Suzanne Ziska
*Assistant Examiner* — Thurman Wheeler
(74) *Attorney, Agent, or Firm* — Browdy and Neimark, PLLC (57) ABSTRACT

A biodegradable, multi-layered controlled release gastroretentive dosage form which is optionally divided into a first dosage of zaleplon for controlled release and a second dosage of zaleplon for immediate release in the stomach and gastrointestinal tract of a patient, folded into a capsule which disintegrates upon contact with gastric juice and the gastroretentive dosage form unfolds rapidly upon contact with gastric juice. The biodegradable, multi-layered gastroretentive dosage forms of the invention provide efficient sleep induction with good sleep maintenance and minimal next day residual effects.

41 Claims, 5 Drawing Sheets

(56) References Cited

OTHER PUBLICATIONS

"Sonata MR" Pipeline Overview and Dynamics Datamonitor, p. 28 (2007).

* cited by examiner

Figure 1

A schematic drawing of the film components of a zaleplon gastroretentive dosage form and their approximate dimensions

Figure 2

Dissolution profile of a 22.5 mg zaleplon gastroretentive dosage form comprising 12.5mg immediate release zaleplon and 10 mg controlled release zaleplon (Example X)

Figure 2:
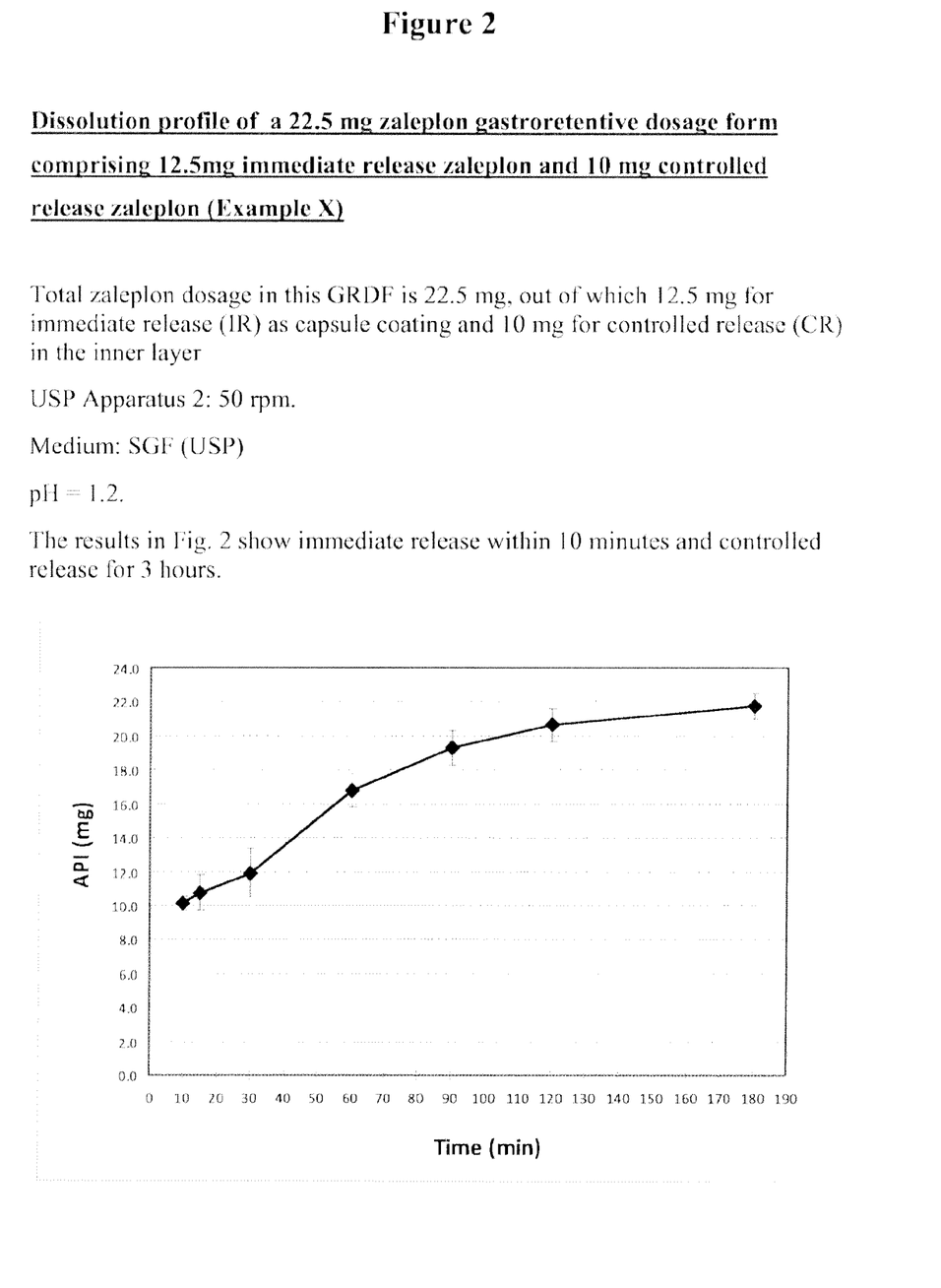
FIG. 2 shows the dissolution profile of a 22.5 mg zaleplon gastroretentive dosage form comprising a combination of 12.5 mg immediate release zaleplon and 10 mg controlled release zaleplon.

Total zaleplon dosage in this GRDF is 22.5 mg, out of which 12.5 mg for immediate release (IR) as capsule coating and 10 mg for controlled release (CR) in the inner layer USP Apparatus 2: 50 rpm.

Medium: SGF (USP)

pH = 1.2.

The results in Fig. 2 show immediate release within 10 minutes and controlled release for 3 hours.

Figure 3

Dissolution profile of a 25 mg zaleplon gastroretentive dosage form comprising 10 mg zaleplon for immediate release and 15 mg for controlled release (Example Y)

Figure 3:
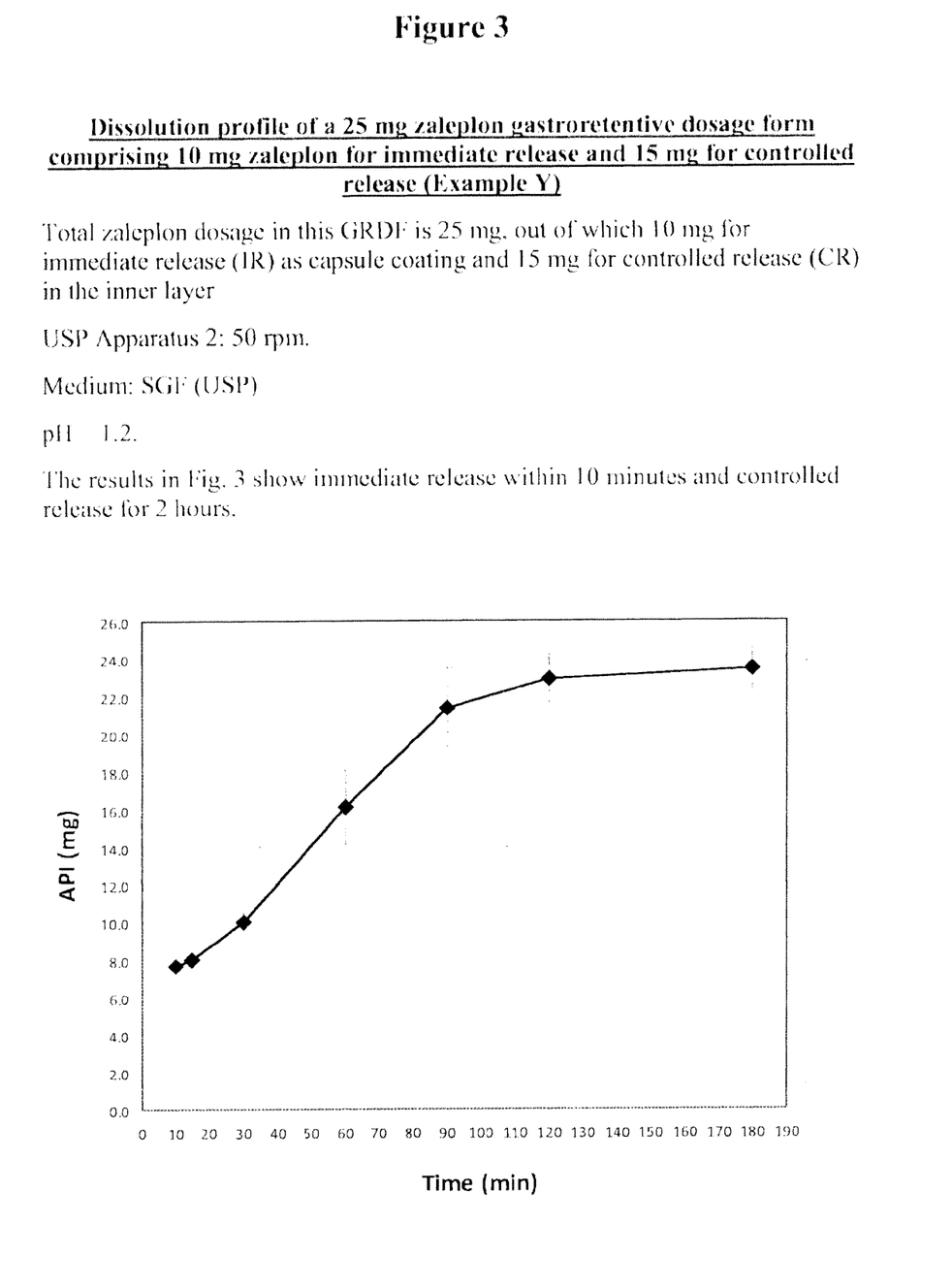
FIG. 3 provides the dissolution profile of a 25 mg zaleplon gastroretentive dosage form comprising a combination of 10 mg immediate release zaleplon and 15 mg controlled release zaleplon.

Total zaleplon dosage in this GRDF is 25 mg, out of which 10 mg for immediate release (IR) as capsule coating and 15 mg for controlled release (CR) in the inner layer USP Apparatus 2: 50 rpm.

Medium: SGF (USP)

pH 1.2.

The results in Fig. 3 show immediate release within 10 minutes and controlled release for 2 hours.

Figure 4

Figure 4:
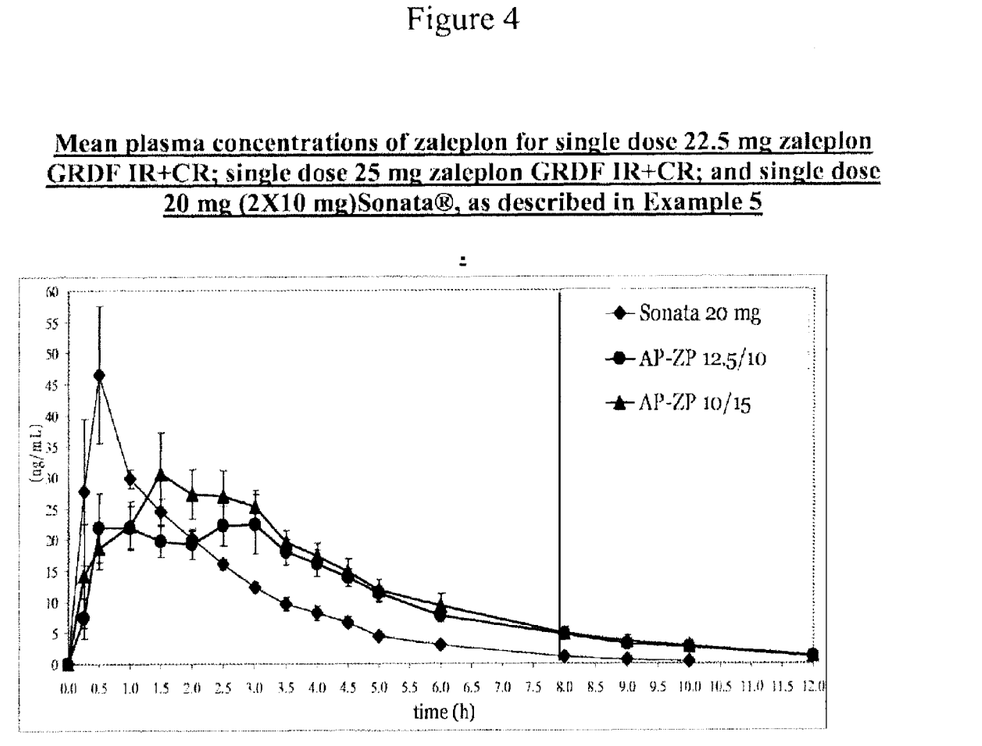
FIG. 4 provides the mean plasma concentrations of zaleplon for a single dose 22.5 mg zaleplon gastroretentive dosage form comprising a combination of 12.5 mg immediate release zaleplon and 10 mg controlled release zaleplon; a single dose 25 mg zaleplon gastroretentive dosage form comprising a combination of 10 mg immediate release zaleplon and 15 mg controlled release zaleplon; and a single dose 20 mg (2×10 mg) immediate release Sonata® formulation, as described in Example 5.

Mean plasma concentrations of zaleplon for single dose 22.5 mg zaleplon GRDF IR+CR; single dose 25 mg zaleplon GRDF IR+CR; and single dose 20 mg (2X10 mg)Sonata®, as described in Example 5

Figure 5

Figure 5:
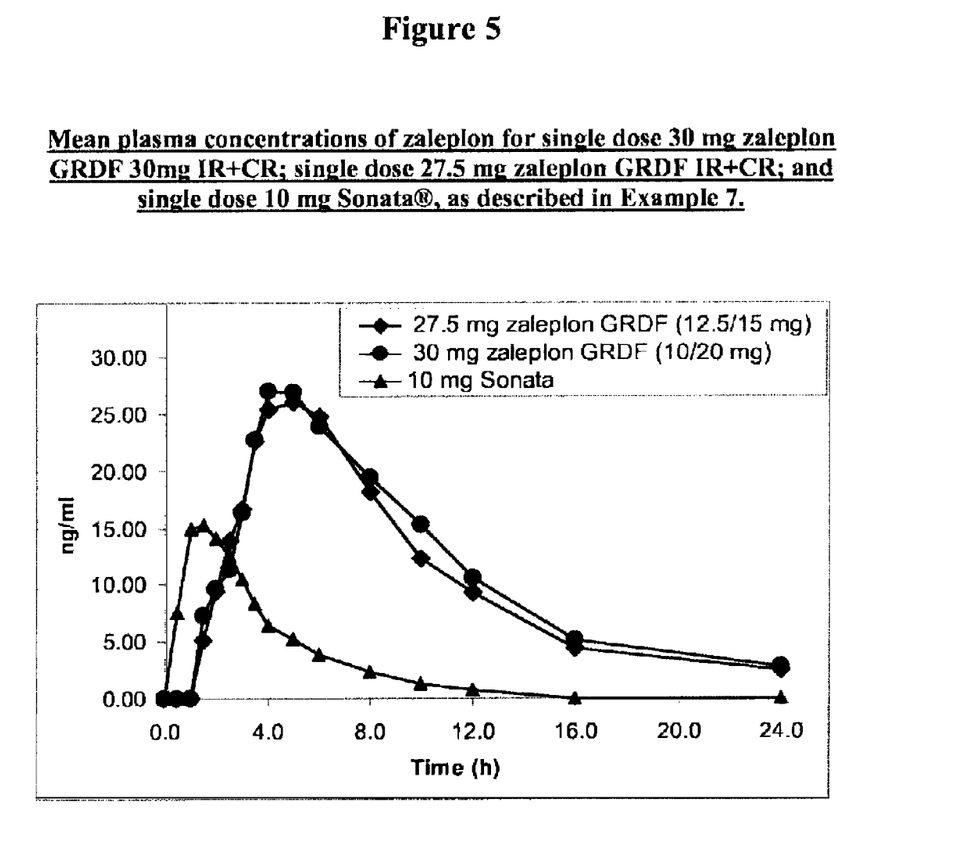
FIG. 5 shows the mean plasma concentrations of zaleplon for a single dose 30 mg zaleplon gastroretentive dosage form comprising a combination of 10 mg immediate release zaleplon and 20 mg controlled release zaleplon; a single dose 27.5 mg zaleplon gastroretentive dosage form comprising a combination of 12.5 mg immediate release zaleplon and 15 mg controlled release zaleplon; and a single dose Sonata® 10 mg immediate release formulation, as described in Example 7.

Mean plasma concentrations of zaleplon for single dose 30 mg zaleplon GRDF 30mg IR+CR; single dose 27.5 mg zaleplon GRDF IR+CR; and single dose 10 mg Sonata®, as described in Example 7.

ZALEPLON GASTRORETENTIVE DRUG DELIVERY SYSTEM

CROSS-REFERENCE TO RELATED APPLICATIONS

The present application claims priority to U.S. Provisional patent Application No. 61/120,051, filed Dec. 4, 2008.

FIELD OF THE INVENTION

The present invention relates to gastroretentive drug formulations for the treatment of insomnia.

BACKGROUND OF THE INVENTION

Insomnia is a common condition which can range from mild to severe and causes people to have trouble falling or staying asleep. The condition may be chronic or acute and leaves the affected subject with little or poor-quality sleep. Lack of sleep may cause other symptoms, such as trouble focusing, anxiety, depression and irritability. One in three adults has insomnia sometimes, and one in ten adults suffers from chronic insomnia.

While acute insomnia is a symptom or side effect of an emotional, neurological, or other medical or sleep disorder, primary or chronic insomnia is its own disorder generally triggered by long-lasting stress or emotional upset.

Lifestyle changes, including better sleep habits, often help relieve acute insomnia. Treatment of chronic insomnia, on the other hand, often requires cognitive-behavioral therapy, which targets the thoughts and actions that can disrupt sleep and focuses on relieving sleep anxiety, and/or the use of short-term or long-term prescription medicines.

Insomnia medicines may often cause side effects, including feeling groggy in the morning, and, rarely, sleep eating, sleep walking, or driving while asleep.

Zaleplon is a short acting, non-benzodiazepine, GABA agonist hypnotic that is indicated for the short-term treatment of insomnia and is commercially available in the US in the form of immediate release 5 mg and 10 mg capsules under the tradename Sonata®.

Zaleplon has a good safety profile. (See Danjou et al. "A comparison of the residual effects of zaleplon and zolpidem following administration 5 to 2 h before awakening" *Br. J. Clin. Pharmacol.* 1999; 48(3):367-74), and has less effect on memory and psychomotor function compared to other drugs, such as zolpidem and zopiclone, even when given at doses much greater than those therapeutically required for the treatment of insomnia.

Sonata® has a maximum plasma concentration (Tmax) of about 1 h (bioavailability percent F is about 30%). Yet, the drug has a very short half life (T0.5=1 h). Thus, although zaleplon has been shown to decrease the time to sleep onset, it has not been shown to increase total sleep time or decrease the number of awakenings. Because of its poor sleep maintenance capabilities, zaleplon commanded in 2007 only 3% of the US insomnia market.

Accordingly, there is an urgent need in the art to develop drugs for the treatment of chronic insomnia with improved sleep maintenance. The present invention satisfies this need.

SUMMARY OF THE INVENTION

It is therefore an object of the invention to provide solutions to the aforementioned deficiencies in the art.

Further to this object, the invention provides a degradable multi-layered gastroretentive dosage form of zaleplon with improved sleep maintenance and minimal residual affects. In one aspect of the invention, the gastroretentive dosage form provides for the controlled release of zaleplon in the stomach and gastrointestinal tract of a patient. In a preferred aspect of the invention, the gastroretentive dosage form of zaleplon comprises a first dosage of zaleplon for immediate release and a second dosage of zaleplon for controlled release, and the gastroretentive dosage form of zaleplon is compacted or folded into a capsule which is easily swallowed and disintegrates rapidly upon contact with gastric juice. Once the capsule disintegrates, the gastroretentive dosage form of zaleplon unfolds rapidly upon contact with the gastric juice. In an even more preferred aspect of the invention, the gastroretentive dosage form of zaleplon which is compacted or folded into a capsule comprises an internal layer comprising a first dosage of zaleplon for controlled release; a rigid frame layer; and one or two outer layers; and the capsule is coated with at least one layer comprising a second dosage of zaleplon for immediate release. In another preferred aspect of the invention, the gastroretentive dosage form of zaleplon which is compacted or folded into a capsule comprises an internal layer comprising a first dosage of zaleplon for controlled release; a rigid frame layer; two outer layers and one or two supra-outer layers comprising a second dosage of zaleplon for immediate release. The capsule disintegrates rapidly upon contact with gastric juice, and the gastroretentive dosage form unfolds rapidly upon contact with the gastric juice.

In one embodiment, the gastroretentive dosage form comprises a dose from about 15 to about 35 mg of zaleplon, divided into a first dosage for immediate release between about 5 and about 15 mg of zaleplon, and a second dosage for controlled-release between about 10 and about 30 mg of zaleplon. In a preferred embodiment, the gastroretentive dosage form comprises a zaleplon dose of 22.5 mg, divided into a dose of 12.5 mg in the coating of the capsule for immediate release, and a dose of 10 mg in the inner layer for controlled-release of zaleplon. In another preferred embodiment, the gastroretentive dosage form comprises a zaleplon dose of 25 mg, divided into a dose of 10 mg in the coating of the capsule for immediate release, and a dose of 15 mg in the inner layer for controlled-release of zaleplon. In a different preferred embodiment, the gastroretentive dosage form comprises a zaleplon dose of 30 mg, divided into two doses of 7.5 mg each in each of the two supra-outer immediate-release layers for immediate release, and a dose of 15 mg in the inner layer for controlled-release of zaleplon.

In one embodiment, the gastroretentive dosage form of zaleplon has two outer layers. In a preferred embodiment, the gastroretentive dosage form of zaleplon comprises two outer layers, each having four orifices, a frame and an inner layer containing zaleplon for controlled release. The gastroretentive dosage form is compacted or folded in a capsule and the capsule is coated with a coating comprising zaleplon for immediate release.

In one embodiment, the outer layer or layers of the gastroretentive dosage forms of zaleplon are perforated in one or more places adjacent to the layer containing the zaleplon to facilitate the release of the zaleplon from the gastroretentive dosage form. Perforations of between about 0.2 and about 2.0 mm may be carried out using a mechanical punch.

In a different embodiment, the gastroretentive dosage form of zaleplon further comprises two supra-outer layers, and containing zaleplon for immediate-release.

In one embodiment, the outer layers in the gastroretentive dosage form of zaleplon are hydratable at a rate greater than the frame layer, and comprise at least one polymeric combination of a hydrophilic polymer and a polymer insoluble in gastric media. In a preferred embodiment, the outer layers comprise one or more types of polymethacrylate USP.

In another preferred embodiment, the outer layers comprise propylene glycol as a plasticizer. In yet another preferred embodiment, the polymeric combination in the outer layers comprises gelatin, and the amount of gelatin is between about 20% and about 45% of the total outer layer composition.

In one aspect of the invention, the outer layer allows passage of gastric media from the environment to the internal layer and inhibits the passage of zaleplon from the internal layer to the environment.

In an additional aspect of the invention, the polymer in the frame layer of the gastroretentive dosage form of zaleplon is a degradable enteric polymer substantially insoluble at pH less than 5.5. The frame layer may, optionally, comprise a plasticizer. In a preferred embodiment, the enteric polymer in the frame layer is selected from the group consisting of cellulose acetate phthalate, hypromellose phthalate, hydroxypropyl methylcellulose acetate succinate, polyvinyl acetate phthalate and methylmethacrylate-methacrylic acid copolymers. In an even more preferred embodiment, the polymer in the frame layer is polymethacrylate copolymer according to the USP-NF (United States Pharmacopeia-National Formulary).

In one embodiment, the frame layer has a mechanical strength described with Young's modulus ranging from about 0.5 to about 15 $Kgf/mm^2$ and a stress of about 0.03 to about 0.6 $Kgf/mm^2$ after 1 hour in simulated gastric fluid.

In a further aspect of the invention, the composition of the frame layer optionally further comprises a filler, a surface-active agent, an additional plasticizer and other suitable materials.

In one embodiment, the inner layer in the gastroretentive dosage form of zaleplon comprises zaleplon and at least one polymer. Zaleplon may be substantially uniformly dispersed in the polymer or may form a solid solution therewith, such that zaleplon is released from the inner layer upon contact of the gastroretentive dosage form with the gastric medium. In one embodiment, the polymer in the inner layer is a water-soluble polymer, which is also soluble in an organic solvent and is capable of increasing zaleplon stability and/or solubility in the aqueous media. In a different embodiment, the polymer is a water-soluble polymer, and is capable of swelling in an aqueous media. In a further embodiment, the inner layer may further comprise at least one plasticizer. In yet another embodiment, the inner layer composition optionally further comprises a filler, a surface-active agent, and/or other suitable materials.

In one aspect of the invention, the inner layer comprises zaleplon in the form of a powder, granulated powder, miniature tablets, coated powder, semisolid composition or any other form known to the skilled in the art.

In one aspect of the invention, a coating comprising at least one layer comprising zaleplon is applied onto the capsule of the gastroretentive dosage form. In one embodiment, the coating comprises at least one polymer, which is preferably instantly soluble in the gastric medium. In an additional embodiment, zaleplon is uniformly dispersed or dissolved in the coating. In a further embodiment, the coating further comprises a plasticizer or a combination of plasticizers. In yet another embodiment, the coating further optionally comprises at least one anti-tacking agent.

In one aspect of the invention, the layers in the gastroretentive dosage form of zaleplon are joined together with ultrasonic welding.

In another aspect of the invention, the outer layer and the frame layer unfold to a length of at least 20 mm within 15 minutes of being exposed to gastric fluid.

In a further aspect of the invention, the gastroretentive drug formulation of zaleplon is fully degradable within 3 hours in simulated intestinal fluid.

In one aspect of the invention, the gastroretentive dosage form of zaleplon optionally comprises an additional layer covering each outer layer and comprising a powder or a film that prevents adherence of the outer layer onto itself when folded inside the capsule. In one embodiment, the layer comprises a powder, a polymer, or a combination thereof.

In another aspect of the invention, the one or two supra-outer layers are affixed to the outer layer on one or two sides of the gastroretentive dosage form. In one embodiment, the supra-outer layers comprise zaleplon and one or more inactive ingredients selected from the group consisting of water soluble polymers, a plasticizer, a solubilizing agent intended for immediate release of the drug in the stomach, a disintegrant and a glidant. In another embodiment, the gastroretentive dosage form of zaleplon optionally comprises an additional layer covering each supra-outer layer. The additional layer comprises a powder or a film or a combination thereof, that prevents adherence of the supra-outer layer onto itself when folded inside the capsule.

In one embodiment, the gastroretentive dosage form of zaleplon has a pharmacokinetic profile similar to that depicted in FIG. 4, curve 12.5/10. In a different embodiment, the gastroretentive dosage form of zaleplon has a pharmacokinetic profile similar to that depicted in FIG. 4, curve 10/15.

In one embodiment, the gastroretentive dosage form of zaleplon provides a mean plasma concentration of zaleplon of about 15 to about 25 ng/ml half an hour after a single dose administration, and the mean plasma concentration remains stable for about 4 to about 5 hours. In a different embodiment, the gastroretentive dosage form of zaleplon provides a mean plasma concentration of zaleplon of about 15 to about 30 ng/ml half an hour after a single dose administration, and the mean plasma concentration remains stable for about 4 to about 5 hours.

In one embodiment, the controlled release gastroretentive dosage form of zaleplon provides a gastric retention period greater than 4 hours. In a preferred embodiment, the controlled release gastroretentive dosage form of zaleplon provides a gastric retention period of up to 12 hours.

In a further aspect, the invention provides a method for providing a therapeutic blood plasma concentration of zaleplon over a period of up to 12 hours resulting in improved sleep maintenance and comprising orally administering to a patient in need thereof a multilayered gastroretentive dosage form of zaleplon. In one aspect of the invention, the method provides a pharmacologically effective blood plasma level of zaleplon from about half an hour to about 12 hours after administration.

In another aspect, the invention provides a method for eliminating sharp peaks in the therapeutic blood plasma concentration of zaleplon after administration of zaleplon to a patient in need thereof over a period of up to 12 hours and improving sleep maintenance, which comprises orally administering to a patient in need thereof a multilayered gastroretentive dosage form of zaleplon.

In yet another embodiment, the invention provides a method for treating insomnia in a patient in need thereof, comprising orally administering one or more gastroretentive dosage forms of zaleplon at bed time or after failing to fall asleep.

In a different aspect, the invention provides a kit comprising a number of gastroretentive dosage forms of zaleplon and instructions and precautions for their use.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

Insomnia is characterized by difficulty in initiating or maintaining sleep, possibly including frequent or prolonged nocturnal awakenings, and is associated with suboptimal quality of sleep. Approximately 50% of adult Americans experience symptoms of insomnia in any given year. The current available therapies for insomnia are mainly focused on sleep induction, and few options are available for sleep maintenance, especially treatments that are not associated with morning residual effects.

The three fundamental attributes that clinicians look for in an insomnia drug are sleep induction, sleep maintenance, and effects on next day function. There are few if any medications that both induce and maintain sleep without having next day hangover or residual effects. There is an urgent clinical need for a drug that will address all these three attributes, cumulatively.

Zaleplon, a non-benzodiazepine hypnotic, is currently indicated for short-term insomnia. The drug is currently characterized by rapid absorption (provides a quick onset of sleep) and rapid elimination which avoids hangover effects, but is associated with poor sleep maintenance.

Zaleplon may be administered at bedtime, later at night after difficulty falling asleep becomes evident, or upon awakening in the middle of the night. The rapid absorption of zaleplon provides a quick onset of sleep for insomnia patients who fail to fall asleep. The rapid elimination of zaleplon avoids daytime sedation and hangover effects. However, because of its short half-life, zaleplon is not effective in maintaining sleep after sleep onset. Once the effect of zaleplon subsides, subjects suffering from insomnia often may wake up in the middle of the night and may need to take another pill. For this reason, there is a great need for a controlled release formulation that can provide steady therapeutic levels.

The present inventors discovered that formulation of zaleplon in gastroretentive dosage form prolongs the absorption phase of the drug throughout the night. The zaleplon gastroretentive dosage forms of this invention are designed to release the zaleplon by a combination of immediate and controlled release mechanisms to provide a quick onset yet a steady level of zaleplon. In particular, oral administration of the zaleplon gastroretentive dosage forms of the invention provides sleep maintenance, preserves the drug's current good sleep induction performance and avoids next-day effects. Accordingly, the invention provides for the first time successful gastroretentive formulations of zaleplon that satisfy the three basic requirements of an optimal insomnia drug: fast sleep induction, extended sleep maintenance and reduced effects on next day function.

In healthy adults a high-fat/heavy meal prolongs the absorption of zaleplon compared to the fasted state, delaying Tmax by approximately 2 hours and reducing Cmax by approximately 35%. Zaleplon AUC and elimination half-life are not significantly affected. These results suggest that the effects of zaleplon on sleep onset may be reduced if it is taken with or immediately after a high-fat/heavy meal. This important aspect is addressed in this invention.

Due to the design flexibility afforded by the complex structure of the gastroretentive dosage forms (GRDFs) of this invention, the GRDFs can conveniently release zaleplon in a sustained profile or in a combined immediate and sustained profile over a prolonged period, while maintaining high drug plasma levels for an extended period of time.

Definitions

As used herein, "Gastroretentive dosage form(s)" (GRDF or GRDFs in the plural) refers to dosage forms with delayed gastric emptying or longer retention in the stomach as compared to food. "Gastroretentive" or "gastric-retentive" dosage forms denote dosage forms comprising multilayer structures including an inner layer, a rigid frame layer and one or two outer layers, or comprising an inner layer, a rigid frame layer, one or two outer layers and one or two supra-outer layers, or comprising the foregoing structures folded or compacted into a capsule. The capsule disintegrates rapidly upon contact with gastric fluid and the structures unfold rapidly upon contact with gastric juice and reside in the stomach of a mammal, preferably a human, for prolonged periods of time, preferably longer than food and small indigestible particles of size below 10 mm in either dimension "Gastric retention" is therefore the maintenance or withholding of a drug in stomach, for a time period longer than the time it would have been retained in the stomach when delivered in a free form or within a gastro-intestinal (GI) delivery vehicle which is not considered gastroretentive. Gastroretentivity may be characterized by retention in the stomach for a period that is longer than the normal emptying time from the stomach, i.e. longer than about 2 hours, particularly longer than about 3 hours and usually more than about 4, 6, 8 or 10 hours. Gastroretentivity typically means retention in the stomach from about 3, 4, 6, 8, 10 or at times 18 hours up to about 21 hours.

"Controlled-release drug delivery system" as used herein denotes a dosage form of zaleplon, which releases zaleplon in a controlled manner over designable time intervals at needed quantities to produce a prolonged, sustained or delayed pharmacological effect that is otherwise unattainable through conventional non-modified-release dosage forms.

"Simulated gastric fluid" ("SGF") and "Simulated intestinal fluid" ("SIF") as used herein refers to "Gastric fluid, Simulated, TS" and "Intestinal fluid, Simulated, TS" solutions as defined by the United States Pharmacopeia 30 National Formulary, without enzymes.

"Gastric medium" and "Intestinal medium" as used herein denote a biological medium of the stomach and intestines, respectively, or an artificial medium, used to mimic the environment of the stomach or intestines.

The term "biodegradable" as used herein is intended as capable of being chemically and/or physically reduced or broken down in the body of a patient and within a relevant time period.

The phrase "polymer which is not instantly soluble in gastric fluid" as used herein refers to a polymer that will gradually dissolve in the GI tract during its residence therein.

The terms "inert" or "inactive" or "inactive ingredient" as used herein refer to components in the internal layer or compartment, outer membranes, optional layers and/or the immediate release layers that do not react with the active ingredient or affect its properties, or cause any biological effect upon administration to a subject.

The phrase "prolonged period" as used herein intends a period of delivery of at least 80% of the dose that lasts for several hours to about 24 hours, usually up to about 12 hours, and often between about 3 and 7 hours.

The terms "swellable" and "swelling" mean, with respect to a polymer, that the polymer is capable of imbibing fluid and expanding when in contact with fluid present in the environment of use.

A "patient" or "subject" as referenced herein is an animal who may receive the gastroretentive drug formulations of the present invention. In a preferred aspect of the invention, the "patient" or "subject" is a human or non-human mammal.

"Treating" or "treatment", and the like are used herein to refer to obtaining a desired pharmacological and physiological effect. The effect may be prophylactic for preventing or partially preventing a disease, symptom or pathological condition and/or may be therapeutic for a partial or complete cure of a disease, condition, symptom or adverse effect attributed to a pathological condition. Thus, "treatment" covers any treatment of a disease in a mammal, particularly a human, and includes: (a) preventing a pathological condition from occurring in an individual which may be predisposed to develop a pathological condition but has not yet been diagnosed as having it, i.e., causing the clinical symptoms of a pathological condition not to develop in a subject that may be predisposed to develop the condition but does not yet experience or display symptoms of the condition; (b) inhibiting, i.e., arresting or reducing the development of the pathological condition or its clinical symptoms; or (c) relieving symptoms associating with the pathological condition.

"Drug", "active pharmaceutical ingredient", "API", "active agent", "active ingredient", "active", and the like, are used in connection with the present invention as pure chemical substances, mixtures of pure chemical substances or crude extracts from various sources, which are used to treat pathological conditions of a person in need or such treatment. "Inactive ingredient", "excipient", "material", "component", "ingredient", "inactive material", "inactive", "agent", and the like as used interchangeably herein, refer to materials or ingredients that are not drugs, but are employed in pharmaceutical compounding in connection with the present invention with intention to impart the final dosage form specific characteristics, as known to the skilled in the art.

"Film" or "layer" or membrane" is used interchangeably in connection with the components of the multi-layered GRDF of this invention and their formulation and preparation is described herein.

As used in the specification and claims, the forms "a", "an" and "the" include singular as well as plural references unless the context clearly dictates otherwise.

Further, as used herein, the term "comprising" is intended to mean that the system includes the recited elements, but not excluding others which may be optional in the design of the system, such as fillers and the like. The term "consisting essentially" of is used to define a system that includes the recited elements but exclude other elements that may have an essential significant effect on the performance of the system. "Consisting of" shall thus mean excluding more than traces of other elements. Embodiments defined by each of these transition terms are within the scope of this invention.

The Zaleplon GRDF of this invention is provided in the form of a capsule containing a multi-layer planar structure composed of films, folded in a wavy way ("accordion"), which unfolds rapidly upon contact with gastric juice and releases zaleplon in the stomach for prolonged time periods. The "accordion" technology has been described in detail in previous publications, for example U.S. Pat. No. 6,685,962, PCT application WP 2007/093999 and PCT application WO07083309, which are incorporated herein by reference in their entirety.

The "accordion" technology, however, cannot uniformly be applied to any drug. Each "accordion" is a product in itself, because different actives require different solutions, due to the different physicochemical properties of the active, the pharmacokinetic requirements, bioavailability, dosages, etc.

Pharmacokinetic requirements specific to each active require different, innovative solutions that fit the specific product. These solutions vary according to case and they may involve different dosages, drug delivery by more than one mechanism (like immediate release and delayed release), with or without supra-outer layers, with or without coating, orifices in various numbers, positions and sizes, different layer compositions, layer thicknesses and sizes and combinations of the above. The possible combinations are endless and success cannot be accurately predicted.

It was an aim of this invention to develop zaleplon GRDFs that would have a rapid onset of action and an extended period of high zaleplon blood levels. Zaleplon posed difficult formulation problems, due to the fact that it is a very slightly soluble drug, according to the USP 30. The inventors of the present application overcome zaleplon formulations problems by devising GRDF formulations that combine the special physicochemical properties of zaleplon, especially its poor solubility, with extended gastric retention, to obtain a zaleplon GRDF that is slowly releasing the active in controlled manner and results in a prolonged hypnotic activity without residual effects.

The Development of Zaleplon GRDFs

The aim of the present invention was to develop a zaleplon GRDF exhibiting a short lag-time and a sustained-release effect over a larger number of hours than the commercial product on the market (Sonata®), but not too long, as to avoid next day residual effects.

Initial attempts to produce zaleplon GRDF (see Example 7 and FIG. 5) showed an increase in the absorption phase of the drug. In order to evaluate the advantages and disadvantages of the initial GRDFs, a clinical study was initiated. Study design was a single center, single-dose, open label, three-way crossover, comparative pharmacokinetic study in healthy volunteers. Evaluation of pharmacokinetic parameters (Cmax, Tmax, and AUC) from plasma concentrations of zaleplon following oral administration of the test formulations as compared to oral administration of Sonata® revealed that the Cmax and Tmax (see FIG. 5) of these GRDFs were significantly higher than in Sonata®.

Combination of a first zaleplon dosage in the inner GRDF layer with a second zaleplon dosage applied as a coating on the GRDF's capsule resulted in zaleplon GRDFs with attractive pharmacokinetic properties. Specific layer formulations, GRDF configurations, layer thicknesses, dosages, orifices and other design and formulation particulars lead to the best results, as detailed herein.

The Zaleplon GRDF Formulations of the Invention

Figure 1:
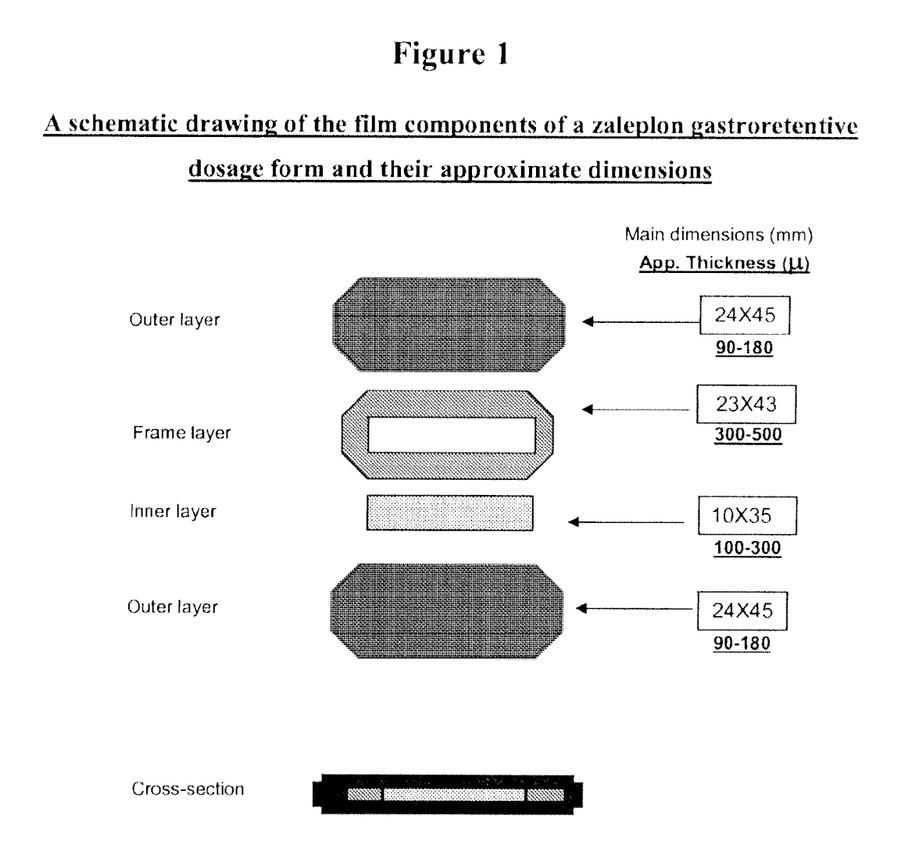
FIG. 1 shows a schematic drawing of the film components of a zaleplon gastroretentive dosage form and their approximate dimensions.

In a preferred embodiment, the zaleplon gastroretentive dosage forms of this invention comprise two outer layers, a frame layer and an inner layer comprising zaleplon and other ingredients for the controlled-delivery of zaleplon. This structure is compacted or folded into a capsule and upon disintegration of the capsule in gastric juice the structure unfolds rapidly upon contact with gastric juice. A schematic of this GRDF is detailed in FIG. 1.

In another preferred embodiment, the zaleplon GRDFs of the invention comprise in addition to the above an external coating of the capsule, comprising a second dose of zaleplon and additional ingredients, for the immediate release of zaleplon.

In yet another preferred embodiment, the Zaleplon GRDFs of the invention comprise, in addition to two outer layers, a frame layer and an inner layer comprising a first zaleplon dose for controlled release, also one or two supraouter layers comprising a second dose of zaleplon and additional ingredients applied externally onto the outer layers, for the immediate release of zaleplon.

In a preferred embodiment, there is provided a degradable multi-layered zaleplon gastroretentive dosage form for the controlled release of zaleplon in the stomach and gastrointestinal tract of a patient compacted or folded into a capsule which disintegrates rapidly and said multilayered zaleplon gastroretentive dosage form unfolds rapidly upon contact with gastric juice, comprising a first dosage of zaleplon for immediate release and a second dosage of zaleplon for controlled release.

In an additional embodiment, the zaleplon gastroretentive dosage form is designed for oral administration and compacted or folded into a standard size capsule which is easily swallowed.

In a preferred embodiment, there is provided a degradable, multi-layered zaleplon gastroretentive dosage form comprising:
a. a first dosage of zaleplon for controlled release in an internal layer;
b. a rigid frame layer; and
c. one or two outer layers;
wherein the above structure is folded into a capsule and the capsule is coated with at least one layer comprising a second dosage of zaleplon for immediate release and upon disintegration of the capsule the gastroretentive dosage form unfolds rapidly upon contact with gastric juice.

In a preferred embodiment, the above zaleplon gastroretentive dosage form has two outer layers.

In another preferred embodiment, the degradable, multi-layered zaleplon gastroretentive dosage form comprises:
a. a first dosage of zaleplon for controlled release in an internal layer;
b. a rigid frame layer;
c. two outer layers; and
d. one or two supra-outer layers comprising a second dosage of zaleplon for immediate release, attached externally to the outer layers,
wherein the gastroretentive dosage form is folded into a capsule which disintegrates rapidly upon contact with gastric juice and, upon disintegration of the capsule, the gastroretentive dosage form unfolds rapidly upon contact with the gastric juice.

In a preferred embodiment, the above zaleplon gastroretentive dosage form has two supra-outer layers.

In another embodiment, the zaleplon dose in the gastroretentive dosage forms of this invention is between 15-35 mg, divided into a first dosage for immediate release between 5-15 mg of zaleplon and a second dosage for controlled-release between 10-30 mg of zaleplon.

In a preferred embodiment, the gastroretentive zaleplon dosage form has a total zaleplon dose of 22.5 mg, divided into an immediate release coating of the capsule containing 12.5 mg of zaleplon and a controlled-release inner layer containing 10 mg of zaleplon (see Example 1).

In a preferred embodiment, the gastroretentive dosage form comprises two outer layers, each outer layer having four orifices, a frame, an inner layer containing zaleplon for controlled release, and the capsule has an immediate release zaleplon-containing coating (see Example 1).

In another preferred embodiment, the gastroretentive dosage form comprises a total zaleplon dose of 25 mg, divided into an immediate release coating of the capsule containing 10 mg of zaleplon and a controlled-release inner layer containing 15 mg of zaleplon (see Example 3).

In yet another embodiment, the gastroretentive zaleplon dosage forms comprise one or two outer layers which are perforated in one or more places adjacent to the layer containing the zaleplon to facilitate the release of the zaleplon into the stomach.

The perforations in the layers of the gastroretentive zaleplon dosage forms may be conveniently carried out with a laser or with a suitably shaped blade and the diameter of the perforations may vary between 0.2-2 mm.

In a preferred embodiment, the gastroretentive dosage form comprises two outer layers, each outer layer having two orifices, a rigid frame, an inner layer containing zaleplon for controlled release, and the capsule has an immediate release zaleplon-containing coating (Example 3).

In another embodiment, the gastroretentive dosage form has a total zaleplon dose of 30 mg, divided between two supra-outer immediate-release layers containing each 7.5 mg of zaleplon and a controlled-release inner layer containing 15 mg of zaleplon (Example 6).

The above gastroretentive dosage form may comprise two supra-outer layers containing zaleplon for immediate-release, two outer layers, each outer layer having four orifices, a rigid frame and an inner layer containing zaleplon for controlled release (Example 6).

In an embodiment, there is provided a gastroretentive dosage form wherein its pharmacokinetic profile is similar to that depicted in FIG. 4, curve 12.5/10.

In another embodiment, there is provided a zaleplon gastroretentive dosage form wherein the mean plasma concentration of zaleplon after a single dose administration reaches about 15-25 ng/ml after about half an hour, and remains in this range for about 4-5 hours.

In yet another embodiment there is provided a zaleplon gastroretentive dosage form wherein its pharmacokinetic profile is similar to that depicted in FIG. 4, curve 10/15.

In a preferred embodiment there is provided a gastroretentive dosage form wherein the mean plasma concentration of zaleplon after single dose administration reaches about 15-30 ng/ml after about half an hour, and remains in this range for about 4-5 hours.

In another embodiment, there is provided a controlled release gastroretentive dosage form where in the zaleplon gastric retention period is greater than 4 hours.

In yet another embodiment there is provided a controlled release gastroretentive dosage form wherein the zaleplon gastric retention period is up to 12 hours.

In a preferred embodiment there is provided a method for providing a therapeutic blood plasma concentration of zaleplon over a period of up to 12 hours resulting in improved sleep maintenance, which comprises orally administering to a subject in need thereof a zaleplon multilayered gastroretentive dosage form, which maintains a pharmacologically effective zaleplon blood plasma level from about half an hour to about 12 hours.

In another preferred embodiment there is provided a method for eliminating sharp peaks in the therapeutic blood plasma concentration of zaleplon after administration of zaleplon to a subject in need thereof over a period of up to 12 hours with improved sleep maintenance which comprises orally administering to the subject a zaleplon multilayered gastroretentive dosage form.

In a preferred embodiment, there is provided a zaleplon gastroretentive dosage form wherein upon administration to a subject in need thereof sleep is rapidly induced with good sleep maintenance and minimal next day residual effects. In another embodiment, there is provided a method of treatment of insomnia in a subject in need thereof comprising administering to the subject one or more zaleplon gastroretentive dosage forms at bed time or after failing to fall asleep.

In yet another embodiment there is provided a kit comprising a number of zaleplon gastroretentive dosage forms and instructions and precautions for their use.

In one embodiment, there is provided a method of treatment of insomnia in a subject in need thereof comprising the zaleplon gastroretentive drug delivery system of this invention. The treatment may be effected by swallowing one or more Zaleplon GRDF capsules of this invention at bed time.

All films, layers and membranes of this invention were made by methods that are well known to those of skill in the art.

In a preferred embodiment, the films (also referred to as "layers") of this invention are prepared by the film casting technique. A solution or suspension of the film composition is cast on trays and dried in an oven until the solvent evaporates. The dried film in then cut according to the needed shape.

In the current embodiments, the gastroretentive dosage form of this invention includes a frame layer, an internal layer and two outer layers. The outer layers are two films which are slightly larger than the frame layer and which are sealed or welded together around their perimeter and completely envelop the frame and the internal layer. Along with welding which connects the outer layers together, the outer portion of the frame layer is also welded to the outer layers. The compositions, ingredients and structure of the various layers forming the GRDF are detailed in the following, illustrative examples.

In one embodiment, the gastroretentive dosage form of this invention has one or two outer layers comprising at least one polymeric combination of a hydrophilic polymer and a polymer insoluble in gastric media, the outer layers being hydratable at a rate greater than the frame layer.

The above polymer in the outer layers is selected from the group consisting of one or more types of polymethacrylate USP.

The outer layers may comprise propylene glycol as a plasticizer.

In one embodiment, the polymeric combination in the outer layers comprises gelatin. The amount of gelatin in the outer layer is between about 20% and about 45% of the total outer layer composition.

In one embodiment, the zaleplon gastroretentive dosage form comprises one or more outer layers, preferably two outer layers permitting passage of gastric media from the environment to the internal layer and inhibiting passage of the zaleplon from the internal layer through the layer to the environment. In other embodiments, the passage of zaleplon from the inner layer to the environment is mediated through dedicated perforations in the said outer layers.

The rigid frame layer of the GRDF (also referred to as "frame" or "backbone") provides mechanical strength to the GRDF.

In one embodiment, there are provided gastroretentive dosage forms wherein the polymer in the frame layer is selected from the group consisting of a degradable enteric polymer which is substantially insoluble at pH less than 5.5 and a plasticizer.

In another embodiment, the polymer in the frame layer of the gastroretentive dosage form is selected from the group consisting of cellulose acetate phthalate, hypromelose phthalate, hydroxypropyl methylcellulose acetate succinate, polyvinyl acetate phthalate and methylmethacrylate-methacrylic acid copolymers.

The polymer in the frame layer may be polymethacrylate copolymer.

The frame layer of the gastroretentive dosage form of this invention has a mechanical strength described with Young's modulus ranging from about 0.5 to about 15 Kgf/mm$^2$ and stress of about 0.03 to about 0.6 Kgf/mm$^2$ after 1 hour in simulated gastric fluid.

The composition of the frame layer may optionally further comprise a filler, a surface-active agent, an additional plasticizer and other materials suitable for such composition.

The inner layer of the GRDF comprises zaleplon and at least one polymer, whereas zaleplon is substantially uniformly dispersed in the polymer or forms a solid solution therewith and wherefrom zaleplon is released upon subjecting the gastroretentive dosage form into a gastric medium, as exemplified in Examples 2 and 3. The at least one polymer is chosen from water-soluble polymers, said polymer preferably soluble in an organic solvent, and said polymer preferably capable of increasing zaleplon stability and/or solubility in aqueous media.

The at least one polymer is chosen from water-soluble polymers, and the polymers are capable of swelling in aqueous media.

The inner layer may further comprise at least one plasticizer.

The inner layer composition may optionally further comprise a filler, a surface-active agent, and/or other materials suitable for such composition.

The gastroretentive dosage form may comprise a zaleplon-comprising coating applied onto the capsule of the gastroretentive dosage form, and the coating comprises at least one layer.

The coating comprises at least one polymer, which is preferably instantly soluble in gastric medium.

Zaleplon in the above coating is uniformly dispersed or dissolved in the coating.

The coating may further comprise a plasticizer or a combination of plasticizers.

The coating may further optionally comprise at least one anti-tacking agent or another filler.

The GRDF layers detailed above are joined together with ultrasonic welding.

The GRDF comprising the outer layers and the frame layer usually unfolds to a length of at least 20 mm within 15 minutes of being exposed to gastric fluid.

The gastroretentive drug formulation is fully degradable within 3 hours in simulated intestinal fluid.

In a preferred embodiment, the gastroretentive dosage form may optionally comprise an additional layer covering each outer layer or each supra-outer layer, comprising a powder or a film that prevents adherence of the outer membrane onto itself when folded inside the capsule, wherein said layer comprises a powder, a polymer, or a combination thereof.

Some of the GRDF of this invention have in addition to the inner layer, frame layer and outer layer or layers, one or two additional external layers, named "supra-outer layers".

In another embodiment, the one or two supra-outer layers are affixed to the outer layer on one or two sides of the gastroretentive dosage form, and the supra-outer layers comprise zaleplon and one or more inactive ingredients selected from the group consisting of polymers, preferably water soluble polymers, a plasticizer, a solubilizing agent intended for immediate release of the drug in the stomach, a disintegrant and a glidant, and any combination of ingredients capable of performing one or more of the said functions.

The detailed description of the present invention is further illustrated by the following examples, which are illustrative only and are not to be construed as limiting the scope of the invention. Variations and equivalents of these examples will be apparent to those skilled in the art in light of the present disclosure, the drawings and the claims herein.

It is appreciated that certain features of the invention which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as prior art to the present invention.

EXAMPLES

Example 1

GRDF-Zaleplon 22.5 mg IR12.5 mg CR10 mg

GRDF type: Immediate Release (IR) capsule coating, Outer-Frame-Inner-Outer (each outer has 4 orifices)

TABLE 1

| IR Coating | (mg per capsule) |
|---|---|
| Triethyl Citrate (TEC) | 2.5 |
| PEG 400 | 1.25 |
| Eudragit E PO | 12.5 |
| Talc Extra fine | 2.5 |
| Zaleplon | 12.5 |

TABLE 2

| Outer Layer | mg |
|---|---|
| Potassium hydroxide | 4.1 |
| Propylene glycol | 63.9 |
| Gelatin (Fish) | 63.9 |
| Eudragit L100-55 | 16 |
| Eudragit L100 | 16 |
| Eudragit S100 | 32 |

TABLE 3

| Rigid Frame Layer | mg |
|---|---|
| Lutrol F127 | 50 |
| Eudragit L100-55 | 29.2 |
| Eudragit L100 | 117.1 |
| Lactose | 62.3 |
| Talc | 15.6 |

TABLE 4

| Inner Layer | mg |
|---|---|
| PEG 400 | 7.5 |
| Kollidon 90 F | 30.0 |
| Methocel E 3 | 10.0 |
| Zaleplon | 10.0 |

Example 2

GRDF-Zaleplon 22.5 mg Release Profile

In order to illustrate the ability of the GRDF to provide both immediate release and controlled release of active ingredient, the release profile of the 22.5 mg Zaleplon GRDF containing 12.5 mg zaleplon in the immediate release coating layer of the capsule and 10 mg in the controlled release internal layer described in Example 1 was determined.

Experiments were conducted in simulated gastric fluid (SGF) in a United States Pharmacopeia (USP) Dissolution Apparatus 2.50 rpm at pH 1.2. As shown in FIG. 2, immediate release occurred within 10 minutes and extended release was seen for 3 hours.

These experiments illustrate the ability of the GRDFs of the invention to effectively deliver zaleplon in an immediate release fashion as well as in a controlled release fashion.

Example 3

GRDF-Zaleplon 25 mg IR10 mg CR15 mg

GRDF type: Immediate Release (IR)—capsule coating, Outer-Frame-Inner-Outer (each outer has 2 orifices)

TABLE 5

| IR Coating | (mg per capsule) |
| --- | --- |
| Triethyl Citrate (TEC) | 2.0 |
| PEG 400 | 1.0 |
| Eudragit E PO | 10.0 |
| Talc Extra fine | 2.0 |
| Zaleplon | 10.0 |

TABLE 6

| Outer Layer | mg |
| --- | --- |
| Potassium hydroxide | 4.1 |
| Propylene glycol | 63.9 |
| Gelatin (Fish) | 63.9 |
| Eudragit L100-55 | 16 |
| Eudragit L100 | 16 |
| Eudragit S100 | 32 |

TABLE 7

| Rigid Frame Layer | mg |
| --- | --- |
| Lutrol F127 | 50 |
| Eudragit L100-55 | 29.2 |
| Eudragit L100 | 117.1 |
| Lactose | 62.3 |
| Talc | 15.6 |

TABLE 8

| Inner Layer | mg |
| --- | --- |
| PEG 400 | 11.25 |
| Kollidon 90 F | 45.0 |
| Methocel E 3 | 15.0 |
| Zaleplon | 15.0 |

Example 4

GRDF-Zaleplon 25 mg Release Profile

In order to illustrate the ability of the GRDF to provide both immediate release and controlled release of active ingredient, the release profile of the 25 mg Zaleplon GRDF containing 10 mg zaleplon in the immediate release coating layer of the capsule and 15 mg in the controlled release internal layer described in Example 3 was determined.

Experiments were conducted in simulated gastric fluid (SGF) in a United States Pharmacopeia (USP) Dissolution Apparatus 2.50 rpm at pH 1.2. As shown in FIG. 3, immediate release occurred within 10 minutes and extended release was seen for 2 hours.

These experiments illustrate the ability of the GRDFs of the invention to effectively deliver zaleplon in an immediate release fashion and in controlled release fashion.

Example 5

Zaleplon GRDF Pharmacokinetic Profiles Compared to Immediate Release Sonata® Pharmacokinetic Profiles in Healthy Subjects A Single-Dose, Three-Way, Nighttime, Crossover Study was performed to Compare the Pharmacokinetics of Gastric retentive Dual release Zaleplon (AP-ZP) Versus Sonata® in 12 Healthy Volunteers. The primary objective was to evaluate the pharmacokinetic parameters (Cmax, Tmax, AUC) from plasma concentrations of zaleplon following oral administration of the test formulations and reference. Study design was a single center, single-dose, open label, three-way crossover, comparative pharmacokinetic study in healthy volunteers.

A) GRDF-ZP 22.5 mg (12.5 mg IR and 10 mg CR)—Example 1
B) GRDF-ZP 25 mg (10 mg IR and 15 mg CR)—Example 3
C) Reference Formulation: Sonata® 20 mg as immediate release, King Pharmaceuticals INC.

All oral formulations were swallowed whole by the volunteers with 240 ml water 3.5 hours after Standardized dinner. Venous blood samples were drawn before dosing and then at frequent intervals to match the pharmacokinetic behavior of the drug. Zaleplon plasma levels were analyzed. The results of the study are shown in the Tables below and in FIG. 4:

TABLE 9

| | | | | 90% Confidence Interval | | |
| --- | --- | --- | --- | --- | --- | --- |
| | AP-A | Sonata® | Ratio | Lower Limit | Upper Limit | P < 0.05 |
| Ln(AUCt) | 111.7 | 102.0 | 1.095 | 1.018 | 1.178 | N |
| ln(AUCI) | 114.5 | 103.2 | 1.110 | 1.025 | 1.201 | N |
| Ln(Cmax) | 29.10 | 45.64 | 0.638 | 0.442 | 0.919 | N |
| Tmax | 1.26 | 0.613 | 2.061 | — | — | N |
| Thalf | 1.89 | 1.41 | 1.345 | — | — | N |

TABLE 10

| | | | | 90% Confidence Interval | | |
| --- | --- | --- | --- | --- | --- | --- |
| | AP-B | Sonata® | Ratio | Lower Limit | Upper Limit | P < 0.05 |
| Ln(AUCt) | 128.3 | 102.0 | 1.258 | 1.170 | 1.353 | Y |
| ln(AUCI) | 131.4 | 103.2 | 1.273 | 1.176 | 1.378 | Y |
| Ln($C_{max}$) | 37.82 | 45.64 | 0.829 | 0.575 | 1.194 | N |
| $T_{max}$ | 2.04 | 0.613 | 3.327 | — | — | N |
| $T_{half}$ | 1.74 | 1.41 | 1.233 | — | — | N |

TABLE 11

| | AP-A | AP-B | Ratio | 90% Confidence Interval | | P < 0.05 |
| --- | --- | --- | --- | --- | --- | --- |
| | | | | Lower Limit | Upper Limit | |
| Ln(AUCt) | 111.7 | 128.3 | 0.871 | 0.809 | 0.936 | Y |
| ln(AUCI) | 114.5 | 131.4 | 0.872 | 0.806 | 0.944 | Y |
| Ln($C_{max}$) | 29.10 | 37.82 | 0.769 | 0.534 | 1.109 | N |
| $T_{max}$ | 1.26 | 2.04 | 0.620 | — | — | N |
| $T_{half}$ | 1.89 | 1.74 | 1.091 | — | — | N |

The results indicate that gastroretentive dual-release delivery of zaleplon yields both quick and steady therapeutic levels. Both gastroretentive dosage forms show comparable or superior bioavailability, in comparison to the immediate-release formulation. The absorption phase was increased to 5 hours in both formulations in comparison to 1 hour of the reference drug. The lack of proportionality of $C_{max}$ in correlation to the dose is evident, and consistent with true controlled-release behavior.

Example 6

GRDF-Zaleplon 30 mg IR15 mg CR15 mg

GRDF type: Immediate Release (IR)—two supra-outer films, Outer-Frame-Inner-Outer (each outer layer has 4 orifices)

TABLE 12

| Outer Layer | mg |
| --- | --- |
| Potassium hydroxide | 4.1 |
| Propylene glycol | 63.9 |
| Gelatin (Fish) | 63.9 |
| Eudragit L100-55 | 16 |
| Eudragit L100 | 16 |
| Eudragit S100 | 32 |

TABLE 13

| Inner Layer | Amount/GRDF (mg) |
| --- | --- |
| Zaleplon | 15.0 |
| Klucel EF (Hydroxypropylcellulose) | 7.5 |
| Klucel GF (Hydroxypropylcellulose) | 7.5 |
| Kollidon K30 (PVP, Povidone) | 3.0 |
| PEG 400 (Polyethyleneglycol) | 1.5 |

TABLE 14

| Rigid Frame Layer | Amount/GRDF (mg) |
| --- | --- |
| Lutrol F127 (poloxamer 407) | 92.5 |
| Eudragit L100 | 212.7 |
| Eudragit L100-55 | 53.2 |
| Lactose | 113.3 |
| Talc | 28.2 |

TABLE 15

| Two Supra-outer Layers | Amount/GRDF (mg) |
| --- | --- |
| Zaleplon | 15.0 |
| Methylcellulose | 18.0 |
| Kollidon K30 (PVP, Povidone) | 30.0 |
| SLS (SDS, Sodium Laurylsulfate) | 15.0 |
| PEG 400 (Polyethyleneglycol) | 8.0 |

Example 7 (Comparative Example)

Pharmacokinetics of a Gastric-Retentive Dual Release (Immediate and Controlled) Formulations of Zaleplon (AP-Zaleplon): Comparison with Immediate-Release Standard Zaleplon (Sonata®)—A Single-Dose, Three-Way, Crossover Study to Compare the Pharmacokinetics of Gastric Retentive Dual Release Zaleplon (AP-ZP) Versus Sonata® in 16 Healthy Volunteers.

The primary objective was to evaluate of pharmacokinetic parameters (Cmax, Tmax, and AUC) from plasma concentrations of zaleplon following oral administration of the test formulations and reference. Study design was a Single center, single-dose, open label, Three-way crossover, comparative pharmacokinetic study in healthy volunteers.
Test Formulation:
GRDF-ZP 27.5 mg (12.5 mg IR and 15 mg CR)
GRDF-ZP 30 mg (10 mg IR and 20 mg CR)—Example 6
Reference Formulation: Sonata® 10 mg as immediate release, King Pharmaceuticals INC.

All oral formulations were swallowed whole by the volunteers with 240 ml water 2.5 hours after a meal and 0.5 hours after a snack to simulate bedtime dosage administration after dinner and an evening snack. Venous blood samples were drawn before dosing and then at frequent intervals to match the pharmacokinetic behavior of the drug. Zaleplon plasma levels were analyzed. The results of the study are shown in FIG. 5.

Both GRDF-Zaleplon formulations showed a significant increase in the absorption phase of the drug.

Example 8

Gastric Retention at Nighttime

The gastric retention performance of the GRDF was tested in an MRI study under similar conditions of the PK study. The GRDF capsules were administered to 10 subjects after a 3 hour fast. Dinner was given 3.5 hours prior to dosing and was eaten within 30 minutes. No additional food was provided until breakfast.

For this study, the drug reservoir layer of the GRDF contained, in place of an active ingredient, iron oxide food coloring (sicovit black e172), which may be visualized in a magnetic resonance imaging (MRI). MRI measurements were taken 2, 4, 6, 8, 10 and 12 hours post dosing.
Summary of Results:

TABLE 16

| No. of subjects which retained GRDF in the stomach after (hours): | | | | | | |
| --- | --- | --- | --- | --- | --- | --- |
| No. of hours | 2 | 4 | 6 | 8 | 10 | 12 |
| No. (out of) | 10(10) | 9(10) | 6(10) | 0(10) | 0(10) | 0(10) |
| % | 100% | 90% | 60% | 0% | 0% | 0% |

What is claimed is:

1. An oral dosage unit for administration of zaleplon, comprising:
   a capsule that disintegrates upon contact with gastric medium following administration, said capsule being coated with a dose of zaleplon for immediate release, and
   a biodegradable multi-layered gastroretentive dosage form that is compacted or folded into said capsule, and, upon disintegration of the capsule, unfolds rapidly upon contact with the gastric medium, wherein said gastroretentive dosage form comprises:
   a. an inner layer comprising a dose of zaleplon for controlled release, the zalephon being substantially uniformly dispersed in a polymer or forming a solid solution therewith, wherein the zaleplon is released from the inner layer upon contact of the gastroretentive dosage form with gastric medium;
   b. a rigid frame layer providing said dosage form with mechanical strength; and
   c. two outer layers, wherein at least one of said outer layers comprises orifices in one or more places adjacent to said inner layer containing zaleplon, said outer layers permitting the passage of gastric medium from the environment,
   wherein the oral dosage unit is constructed and dosed such that, upon administration to a subject, a pharmacologically effective blood plasma level of zaleplon is maintained from about one half hour following administration through about four to about twelve hours.

2. The oral dosage unit of claim 1, comprising a dose of 22.5 mg of zaleplon, of which 10 mg are contained in said inner layer for controlled release of the zaleplon and 12.5 mg are contained in the coating on the capsule for immediate release of zaleplon.

3. The oral dosage unit of claim 1, wherein the diameter of the orifices is between about 0.2 and about 2 mm.

4. The oral dosage unit of claim 1, wherein each of the two outer layers has two orifices.

5. The oral dosage unit of claim 2, wherein, upon administration to a subject, zaleplon released from the oral dosage unit provides a pharmacokinetic profile which is comparable to the pharmacokinetic profile depicted in FIG. 4, curve 12.5/10.

6. The oral dosage unit of claim 2, which provides a mean plasma concentration of about 15 to about 25 ng/ml of zaleplon within about half an hour after a single dose administration, and wherein the mean plasma concentration remains constant for about 4 to about 5 hours.

7. The oral dosage unit of claim 1, which provides a zaleplon gastric retention period greater than 4 hours.

8. The oral dosage unit of claim 1, which provides a zaleplon gastric retention period of up to 12 hours.

9. The oral dosage unit of claim 1, wherein the outer layers are hydratable at a rate greater than the frame layer; and wherein the outer layers comprise at least one polymeric combination of a hydrophilic polymer and a polymer insoluble in gastric media.

10. The oral dosage unit of claim 9, wherein the polymer insoluble in gastric media is selected from the group consisting of one or more types of polymethacrylate USP.

11. The oral dosage unit of claim 9, wherein the outer layers comprise propylene glycol as a plasticizer.

12. The oral dosage unit of claim 9, wherein the polymeric combination in the outer layers comprises gelatin.

13. The oral dosage unit of claim 12, wherein the amount of gelatin in the outer layers is between about 20% and about 45% of the total outer layer composition.

14. The oral dosage unit of claim 1, wherein the rigid frame layer comprises a polymer, the polymer optionally being a degradable enteric polymer which is substantially insoluble at pH less than 5.5, and wherein the rigid frame layer further comprises a plasticizer.

15. The oral dosage unit of claim 14, wherein the enteric polymer in the rigid frame layer is selected from the group consisting of cellulose acetate phthalate, hypromellose phthalate, hydroxypropyl methylcellulose acetate succinate, polyvinyl acetate phthalate and methylmethacrylate-methacrylic acid copolymers.

16. The oral dosage unit of claim 14, wherein the polymer in the rigid frame layer is a polymethacrylate copolymer USP.

17. The oral dosage unit of claim 14, wherein the rigid frame layer has a mechanical strength described with Young's modulus ranging from about 0.5 to 15 $Kgf/mm^2$ and stress of about 0.03 to about 0.6 $Kgf/mm^2$ after 1 hour in simulated gastric fluid.

18. The oral dosage unit of claim 14, wherein the frame layer further comprises a filler, a surface-active agent, and an additional plasticizer.

19. The oral dosage unit of claim 1, wherein the at least one polymer of the inner layer is selected from the group consisting of: a water soluble polymer, a polymer that is soluble in water and in an organic solvent, and a polymer that is capable of increasing zaleplon stability and/or solubility in aqueous media.

20. The oral dosage unit of claim 1, wherein the at least one polymer of the inner layer is a water-soluble polymer capable of swelling in aqueous media.

21. The oral dosage unit of claim 1, wherein the inner layer further comprises at least one plasticizer.

22. The oral dosage unit of claim 1, wherein the inner layer further comprises at least one of a filler and a surface active agent.

23. The oral dosage unit of claim 1, wherein the inner layer comprises zaleplon in a form selected from the group consisting of a powder, granulated powder, miniature tablets, coated powder, semisolid composition and combinations thereof.

24. The oral dosage unit of claim 1, wherein the coating on the capsule comprises at least one layer.

25. The oral dosage unit of claim 24, wherein the coating comprises at least one polymer which is instantly soluble in gastric medium.

26. The oral dosage unit of claim 24, wherein zaleplon is uniformly dispersed or dissolved in the coating on the capsule.

27. The oral dosage unit of claim 24, wherein the coating on the capsule further comprises a plasticizer or a combination of plasticizers.

28. The oral dosage unit of claim 24, wherein the coating on the capsule further comprises at least one anti-tacking agent.

29. The oral dosage unit of claim 1, wherein the inner layer, the frame layer and the two outer layers are joined together with ultrasonic welding.

30. The oral dosage unit of claim 1, wherein the gastroretentive dosage form unfolds to a length of at least 20 mm within 15 minutes of being exposed to gastric fluid.

31. The oral dosage unit of claim 1, wherein the gastroretentive dosage form is fully degradable within 3 hours in simulated intestinal fluid.

32. The oral dosage unit of claim 1, comprising a dose of zaleplon from about 15 to about 35 mg, of which from about 10 to about 30 mg of zaleplon are contained in said inner layer for controlled-release of zaleplon, and from about 5 to about 15 mg are contained in said coating on the capsule for immediate-release of zaleplon.

33. The oral dosage unit of claim 1, comprising a dose of 25 mg of zaleplon, of which 15 mg are contained in said inner layer for controlled release of the zaleplon and 10 mg are contained in said coating on the capsule for immediate release of zaleplon.

34. The oral dosage unit of claim 33, wherein, upon administration to a subject, zaleplon released from the dosage form provides a pharmacokinetic profile which is comparable to the pharmacokinetic profile depicted in FIG. 4, curve 10/15.

35. The oral dosage unit of claim 33, which provides a mean plasma concentration of about 15 to about 30 ng/ml of zaleplon within about half an hour after a single dose administration, and wherein the mean plasma concentration remains stable for about 4 to about 5 hours.

36. The oral dosage unit of claim 1, wherein each of the two outer layers has four orifices.

37. The oral dosage unit of claim 1, further comprising an additional layer covering each outer layer, comprising a powder or a film that prevents adherence of the outer layer onto itself when folded inside the capsule, wherein the additional layer comprises a powder, a polymer, or a combination thereof.

38. A kit comprising a number of zaleplon oral dosage units of claim 1 and instructions and precautions for their use.

39. A method for providing a therapeutic blood plasma concentration of zaleplon over a period of up to 12 hours resulting in improved sleep maintenance, which comprises orally administering to a subject in need thereof a zaleplon oral dosage unit of claim 1, wherein the oral dosage unit provides a therapeutically effective blood plasma level of zaleplon from about half an hour to about 12 hours after administration.

40. A method for eliminating sharp peaks in the therapeutic blood plasma concentration of zaleplon after administration of zaleplon to a subject in need thereof over a period of up to 12 hours and improving sleep maintenance, which comprises orally administering to the subject a zaleplon oral dosage unit of claim 1.

41. A method for treating insomnia in a subject in need thereof, comprising orally administering one or more oral dosage unit of claim 1 at bed time or after failing to fall asleep.

* * * * *